United States Patent [19]

Harris et al.

[11] Patent Number: 5,482,931
[45] Date of Patent: Jan. 9, 1996

[54] STABILIZED PHARMACEUTICAL PEPTIDE COMPOSITIONS

[75] Inventors: Alan Harris; Birgitta Tennhammar-Ekman, both of Malmo, Sweden

[73] Assignee: Ferring AB, Malmo, Sweden

[21] Appl. No.: 84,563

[22] Filed: Jun. 29, 1993

[51] Int. Cl.$^6$ .......................... A61K 38/00; C07K 14/00; C07K 7/16
[52] U.S. Cl. .................... 514/15; 514/2; 514/12; 530/315
[58] Field of Search ..................... 514/2, 12, 15

[56] References Cited

U.S. PATENT DOCUMENTS

| | | |
|---|---|---|
| 3,794,633 | 2/1974 | Kamber et al. . |
| 3,929,758 | 12/1975 | Hughes et al. . |
| 4,033,940 | 7/1977 | Hughes et al. . |
| 4,093,610 | 6/1978 | Abraham et al. . |
| 4,216,141 | 8/1980 | Rivier et al. . |
| 4,271,068 | 6/1981 | Kamber et al. . |
| 4,351,764 | 9/1982 | Birr . |
| 4,487,765 | 12/1984 | de Wied . |
| 4,764,378 | 8/1988 | Keith et al. ........................ 424/435 |
| 4,985,242 | 1/1991 | Sekine et al. ........................ 514/12 |
| 5,066,716 | 11/1991 | Robey et al. . |
| 5,124,315 | 6/1992 | Ceschel et al. ........................ 514/12 |

FOREIGN PATENT DOCUMENTS

| | | |
|---|---|---|
| PCTWO93/03744 | 3/1993 | European Pat. Off. . |
| 1900367 | 9/1969 | Germany . |
| 2254043C2 | 1/1985 | Germany . |
| 3335086C2 | 9/1990 | Germany . |
| 0199922 | 11/1986 | United Kingdom . |

Primary Examiner—Jill Warden
Assistant Examiner—S. G. Marshall
Attorney, Agent, or Firm—Hopgood, Calimafde, Kalil & Judlowe

[57] ABSTRACT

Disclosed is a stabilized aqueous composition for administration to a patient comprising a biologically active peptide, a buffer, a quaternary amine-type preservative or disinfectant, and an osmotic pressure-controlling agent, which composition can be stored and used at room temperature. The buffer stabilizes the pH of the composition between about 4 and 6. The preferred buffer contains citrate and/or phosphate, and the preferred preservative or disinfectant is benzalkonium chloride. The composition protects the peptide contained therein from adhering to container surfaces, particularly in containers made of polymeric materials.

22 Claims, 1 Drawing Sheet

STABILIZED PHARMACEUTICAL PEPTIDE COMPOSITIONS

FIELD OF THE INVENTION

The present invention relates to stabilized aqueous pharmaceutical compositions for nasal, oral or parenteral administration of small and medium-size peptides (up to about eicosapeptides), such as desmopressin (1-deamino-8-D-arginine vasopressin; DDAVP).

BACKGROUND

As used herein, the term "stabilized composition" refers to an aqueous solution for therapeutic use, containing at least one small or medium-size biologically active peptide. Such stabilization should allow the composition to be stored at room temperature for extended periods without loss in biological activity.

A substantial number of biologically active peptides, their derivatives and analogs (in the following termed "peptides") are known to be therapeutically useful. For various reasons they are often administered in form of aqueous compositons, that is, sterile aqueous solutions containing a known amount of peptide.

The biological activity of the peptides to be administered is often extremely high. Thus, only very small amounts of peptide are needed for a single does. Such dilute aqueous peptide solutions in general are not stable at room temperature for longer periods, even if kept in sealed containers. The therapeutically active peptide hormone analog desmopressin is such a peptide. Its aqueous solution has to be stored at a temperature not exceeding 8° C. Storage at higher temperaturs such as, for instance, room temperature, results in the degradation of desmopressin by hydrolytic and/or oxidative processes which are not blocked by the addition of a preservative, such as chlorobutanol (1,1,1-trichloro-2-methylpropan-2-ol). However, chlorobutanol effectively protects desmopressin against microbial attack.

Another problem with dilute aqueous solutions of peptides is the adsorption of minute amounts of peptide to the walls of the container in which the solution is kept. Since such peptide solutions are usually very dilute, adsorption of even minor amounts may substantially reduce the amount of peptide available for administration.

A particularly attractive way of administration of small and medium-size peptides in solution is via the nasal mucosa, either as drops or in spray form, which is even more convenient and more reproducible. Desmopressin, for instance, can be administered in an aqueous, 0.9 % sodium chloride solution (saline) by this route.

Various kinds of intranasal spray delivery devices are known in the art. In general, peptides in an aqueous solution are administered by means of metered-dose spray pumps, such as those manufactured by Ing. Erich Pfeiffer KG, Radolfzell, Germany. An alternate route is via a graduated plastic tube of special design called a "rhinyle" which is partially filled with an aqueous solution containing a peptide. One end of the rhinyle is placed in the mouth and the other end is placed in the desired nostril, The solution is then delivered to the nostril by blowing.

Peptides for nasal administration often have extremely high biological activity, and only a very small amount of peptide is needed in a single dose. However, the particular form of administration may require a minimum liquid volume for good reproducibility. Thus, effective concentration ranges for nasally administered peptides are generally quite low. For instance, a single desmopressin dose for nasal administration is typically between 10 µg to 40 µg, but may even be as little as 2.5 µg and as high as 300 µg. Typical dose volumes are from 100 µl to 400 µl (4×100 µl). These doses are normally taken on a regular basis, such as at least once daily.

OBJECTS OF THE INVENTION

Thus, it is an object of the present invention to overcome the aforementioned stability and storage problems associated with known aqueous solutions of small and medium size peptides, particularly of aqueous solutions containing desmopressin.

Another object is to provide a stabilized aqueous solution containing a peptide for nasal, oral or parenteral administration which can be conveniently stored at room temperature for extended periods of time, for instance, one year, without risking partial or total degradation or microbial contamination of the peptide contained therein.

A further object is to protect the peptide in solution from adhering to the walls of the container without using extraneous additives specifically designed for that purpose.

Yet another object is to provide an aqueous nasal or drop spray composition for the management of diseases and abnormal conditions which are mitigated by administration of small and medium sized, biologically active peptides.

SUMMARY OF THE INVENTION

The present invention is an aqueous composition for administration of small and medium-size peptides, particularly desmopressin, which can maintain stability over time and at room temperature, active biological ingredients carried therein such as a peptide, an analog of a peptide or mixtures of peptides and/or their analogs. The solution contains a buffer, a quaternary amine preservative or disinfectant and an osmotic pressure-controlling agent.

The quaternary amine preservative or disinfectant selectively used have, in addition to their namesake functions, the unexpected ability to prevent adsorption of small and medium size peptide components from adhering to container walls, particularly walls of containers made of polymeric materials.

It is preferred for the peptide or peptide analog to be oxytocin or vasopressin, or their analogs and derivatives, such as particularly preferred, desmopressin (hereinafter also "DDAVP").

Also preferred are terlipressin (N-α-triglycyl-8-lysine)-vasopressin), atosiban ((Mpa$^1$, D-Tyr(Et)$^2$, Thr$^4$, Orn$^8$)-oxytocin), carbetocin ((1-desamino-1-monocarba-2(0-methyl)-tyrosine)-oxytocin) and triptorelin [D-Trp$^6$]-LHRH.

It is preferred for the buffer to be capable of maintaining a pH of between 4.0 and 6.0. Especially preferred is a pH of about 5.0.

In one embodiment, the buffer used is acetic acid/sodium acetate. It is preferred for the stabilized peptide solution according to the invention to contain citrate and/or phosphate. Preferred buffer systems according to the invention are citric acid/disodium hydrogen phosphate, sodium dihydrogen phosphate/disodium hydrogen phosphate, and citric acid/sodium citrate. Specifically preferred is a buffer comprising: citrate-phosphate-sodium ions in a molar ratio of from about 1:3:3 to about 1:1:2.

It is preferred for the quaternary amine preservative or disinfectant to be benzalkonium chloride, $(NR^1R^2R^3R^4)^+$ $Cl^-$; where $R^1$, $R^2$=methyl, $R^3$=benzyl, $R^4=C_8H_{17}$ to $C_{18}H_{37}$. The composition according to the invention preferably contains the quaternary amine preservative or disinfectant in a concentration from about 0.05 to about 0.2 mg per ml. Particularly preferred is a concentration of about 0.1 mg per ml.

It is preferred for the osmotic pressure-controlling agent to be sodium chloride. The buffer components also contribute substantially to osmotic pressure control.

According to a preferred aspect of the invention the composition additionally contains at least one mucosal absorption enhancer such as bile salts, monolauryl ethers of macrogols, phospholipids, and fusidate derivatives.

A preferred embodiment of the composition according to the invention contains from 0.025 mg to 1.5 mg of desmopressin acetate, from 1.35 to 1.75 mg of citric acid, from 2.25 to 2.65 mg of disodium hydrogen phosphate, from 0.05 to 0.20 mg benzalkonium chloride, and sodium chloride in an amount sufficient to provide the overall solution with an osmotic pressure comparable to that of human plasma.

According to another preferred embodiment of the invention, there is also disclosed the use of an aqueous spray composition for the management of diseases and abnormal conditions that can be treated by nasal administration of small and medium-size peptides.

DETAILED DESCRIPTION

Figure 1:
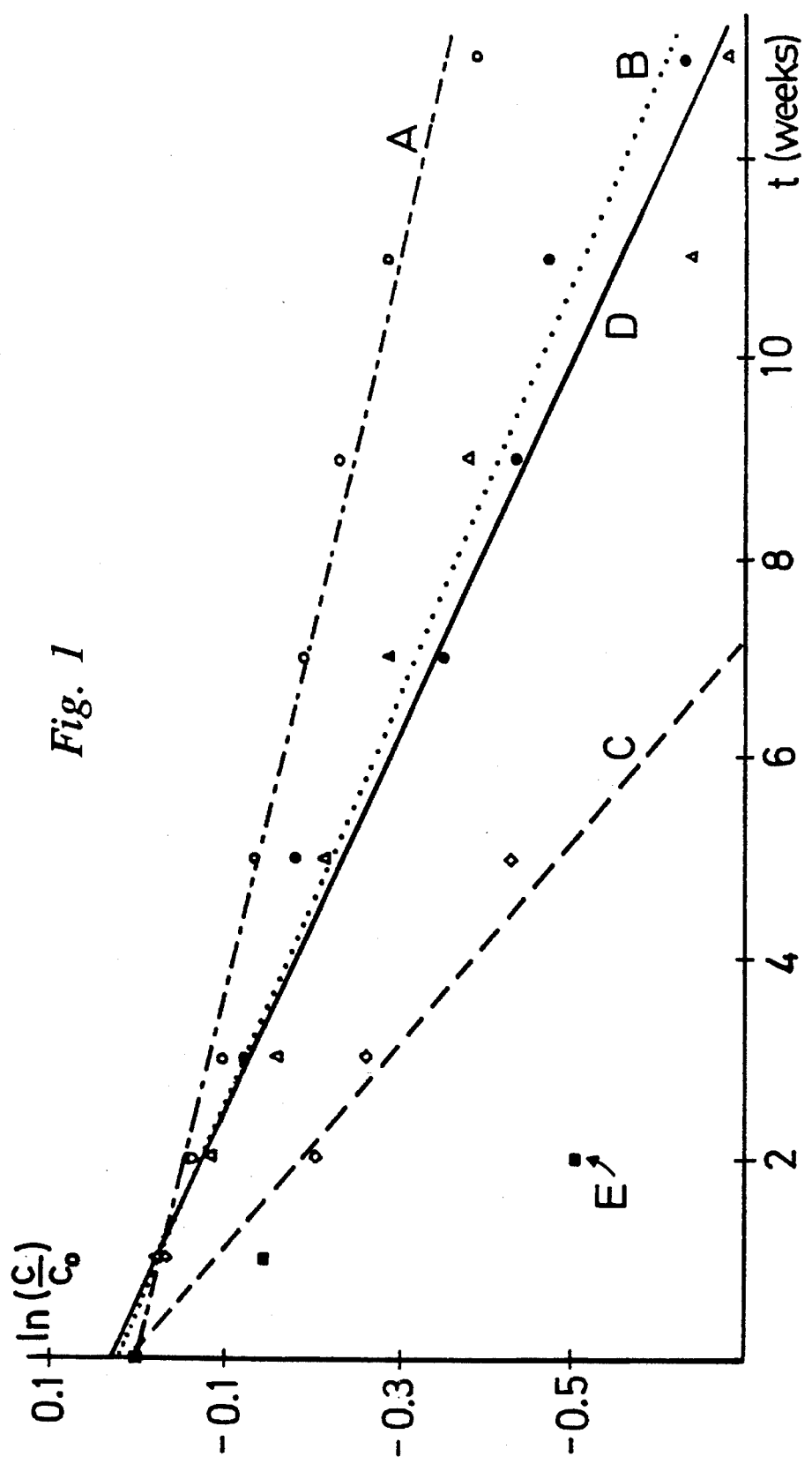
FIG. 1 graphically illustrates the results of stability testing for the compositions prepared according to the present invention.

The invention will now be explained in more detail by reference to the following experimental examples:

Example 1

PREPARATION OF TEST COMPOSITIONS

Five test compositions containing desmopressin (DDAVP) acetate for nasal spray or drop compositions containing various preservatives were prepared, compositions A, B, C, D and E (see Table 1). Each test sample contained 0.089 mg DDAVP free base per ml, and Table 1 denotes the type of buffer used in each system. Millipore®-filtered water was used as solvent.

Compositions A and B were prepared according to the present disclosure. Compositions C, D and E were prepared for comparative testing of other preservatives.

The stability of the known, unbuffered Minirin® (DDAVP) spray containing NaCl and chlorobutanol has a useful shelf life of 3 years at refrigerated storage when kept in sealed glass containers. It is not stable at room temperature when stored for longer periods of time. Note that composition E contains NaCl and chlorobutanol, but is a buffered solution.

TABLE 1

Stabilized desmopressin compositions (amounts per ml)
A and B denote compositions according to the invention;
C, D, E denote compositions prepared for comparison

| Composition | NaCl mg | BH mg (mmol) | B⁻Na⁺ mg | preservative mg |
|---|---|---|---|---|
| A | 8.74 | AcOH (mmol) 2.96 · 10³ | NaOAc 0.58 | benzalkonium chloride, 0.1 |
| B | 6.29 | citric acid 1.56 | Na₂HPO₄ 2.43 | benzalkonium chloride, 0.1 |
| C | 5.24 | citric acid 1.97 | Na₂HPO₄ 1.83 | benzyl alcohol 10.0 |
| D | 6.30 | citric acid 1.56 | Na₂HPO₄ 2.43 | methyl p-hydroxy-benzoate*, 0.80 propyl p-hydroxy-benzoate**, 0.20 |
| E | 5.64 | citric acid 1.97 | Na₂HPO₄ 1.83 | chlorobutanol 5.00 |

*methyl paraben; **propyl paraben

Example 2

STABILITY TESTING BY DETECTING PEPTIDE DEGRADATION

The DDAVP-compositions prepared in Example 1 were stored in 10 ml glass vials (hydrolytic class 1, provided with Teflon® stoppers) in the dark at 65° C. for up for 13 weeks. Samples were taken after 1, 2, 3, 5, 7, 9, 11, and 13 weeks and analyzed for DDAVP by HPLC [Varian Star system; Lichrospher® PR-18 5 μm column (50×4 mm); gradient elution with various proportions of acetonitrile/0.0667M aqueous phosphate buffer pH The results are graphically depicted in FIG. 1 and demonstrate the superior stabilizing effect of the composition according to the invention. The experimental data contained in FIG. 1 were also used for calculation of first order rate constants shown in Table 2, below.

TABLE 2

First order rate constants for degradation of desmopressin

| Composition | k (s⁻¹) | correlation coefficient |
|---|---|---|
| A | 4.6 · 10⁻⁸ | 0.98 |
| B | 8.0 · 10⁻⁸ | 0.98 |
| C | 1.6 · 10⁻⁷ | 0.97 |
| D | 8.8 · 10⁻⁸ | 0.96 |
| E | ~9 · 10⁻⁷ | 0.83 |

Example 3

CALCULATION OF USEFUL SHELF-LIFE

From the slopes of the curves in FIG. 1 and from corresponding storage tests carried out at 37° C., 50° C., and 60° C. Arrhenius activation energies ($E_a$) were obtained for compositions A, B, C and D. Composition E did not show Arrhenius-type behaviour since it was the least stable composition by far.

The storage time over which total DDAVP content of each composition was reduced by 10% ($t_{90}$) at 25° C. and 30° C., "useful shelf life", was calculated from $E_a$ which is tabulated below in Table 3.

TABLE 3

Useful shelf life in years ($t_{90}$) for stabilized desmopressin compositions

| Composition | activation energy ($E_a$, kJ/mol) | $t_{90}$ 25° C. | 30° C. |
|---|---|---|---|
| A | 123.5 | 27.0 | 11.9 |
| B | 115.1 | 12.9 | 6.0 |
| C | 115.5 | 5.7 | 2.7 |
| D | 102.8 | 7.4 | 3.7 |

As Table 3 shows, desmopressin is preserved in compositions A and B for extended periods of time at room temperature, thus demonstrating the ability of the present invention to be stored and used for extensive periods without refrigeration.

Example 4

COMPARISON OF INTRA-NASAL DESMOPRESSIN UPTAKE 24 healthy fasting male subjects were given (randomized) desmopressin (20 µl) intransally in spray form (200 µl), using either compositon B or the commercially available unbuffered Minirin® formulation containing chlorobutanol as preservative. Blood samples were collected at intervals and desmopressin plasma levels monitored over a 12 h period by a desmopressin-specific RIA plasma assay (Lundin, S. et al., Acta Endocrinologica (Copenhagen) 108 (1985) 170–183). Essentially the same desmopressin plasma level profile was found for the two compositions.

This is an unexpected result since H. A. Batts et al. (J. Pharm. Pharmacol. 1989, 156–159) found that chlorobutanol and benzalkonium chloride differed significantly in their effect on the mucociliary transport rate in a frog palate model. The rate of mucociliary clearance affects the comparatively slow intra-nasal uptake of peptides and other nasally administered biologically active compounds.

Example 5

ABSORPTION-BLOCKING EFFECT OF DESMOPRESSIN

Sterile aqueou solutions of desmopressin marked with $^{125}I$ (appr. 10,000 CPM/ml) containing benzalkonium chloride+saline, chlorobutanol+saline, or saline only, were all incubated in tubes of polystyrene, polypropene and glass for 24 h at ambient temperature.

In the solutions containing benzalkonium chloride and chlorobutanol, respectively, desmopressin showed insignificant adsorption, whereas only about half of the amount of desmopressin in the preservative-free solution could be recovered from the plastic tubes.

While the various features and embodiments of the present invention have been described herein, it is possible that one skilled in the art could modify the various aspects of the invention and obtain the same objectives. The present disclosure contemplates such modifications as being within its spirit and scope.

What is claimed is:

1. A stable, aqueous composition for administration to a patient of at least one biologically active peptide, consisting essentially of:
   a) said biologically active peptide selected from the group consisting of oxytocin, vasopressin, an oxytocin analog, an oxytocin derivative, a vasopressin analog, and a vasopressin derivative;
   b) a buffering agent;
   c) a quaternary amine preservative or disinfectant; and
   d) an osmotic pressure-controlling agent.

2. The composition according to claim 1, wherein said peptide is selected from the group consisting of terlipressin, atosiban, carbetocin, and triptorelin.

3. The composition according to claim 1, wherein said vasopressin analog is desmopressin.

4. The composition according to claim 1, wherein said buffering agent is a buffer which maintains the pH of said composition between 4.0 and 6.0.

5. The composition according to claim 4, wherein said buffer maintains said pH at about 5.0.

6. The composition according to claim 1, wherein said buffering agent comprises a buffer selected from the group consisting of citrate, phosphate, and a mixture of citrate and phosphate.

7. The composition according to claim 6, wherein said buffer mixture of citrate and phosphate contains sodium ions such that the molar ratio of citrate, phosphate and sodium ions is from about 1:3:3 to about 1:1:2.

8. The composition according to claim 1, wherein said quaternary amine preservative or disinfectant is benzalkonium chloride having the following structure:

$$(NR^1R^2R^3R^4)^+Cl^-$$

where $R^1$ and $R^2$ are both methyl; $R^3$ is benzyl; and $R^4$ can be an alkyl group from $C_8H_{17}$ to $C_{18}H_{37}$.

9. The composition according to claim 1, wherein said administration is oral.

10. The composition according to claim 1, wherein said administration is parenteral.

11. An aqueous composition for nasal administration of a biologically active component, consisting essentially of:
   a) said biologically active component selected from the group consisting of a peptide selected from the group consisting of oxytocin, vasopressin, an oxytocin analog, an oxytocin derivative, a vasopressin analog, and a vasopressin derivative;
   b) a buffering agent;
   c) a quaternary amine preservative of disinfectant; and
   d) an osmotic pressure-controlling agent such the said composition is capable of maintaining said biologically active component in a functionally stable condition over extended periods and at room temperature.

12. The composition of claim 11, wherein said vasopressin analog is desmopressin.

13. The composition according to claim 11, wherein said buffering agent is a buffer which maintains the pH of said composition between 4.0 and 6.0.

14. The composition according to claim 13, wherein said buffer maintains said pH at about 5.0.

15. The composition of claim 11, wherein said buffering agent comprises a buffer selected from the group consisting of citrate, phosphate, and a mixture of citrate and phosphate.

16. The composition of claim 15, wherein said buffer comprises a mixture of citrate and disodium hydrogen phosphate such that the molar ratio of citrate, phosphate and sodium ions is from about 1:3:3 to about 1:1:2.

17. The composition according to claim 11, wherein said quaternary amine preservative or disinfectant is benzalkonium chloride having the following structure:

$$(NR^1R^2R^3R^4)^+Cl^-$$

where $R^1$ and $R^2$ are both methyl; $R^3$ is benzyl; and $R^4$ can be an alkyl group from $C_8H_{17}$ to $C_{18}H_{37}$.

18. A stable aqueous composition for nasal application, comprising:
   a) from 0.025 mg to 1.5 mg of desmopressin acetate;
   b) from 1.35 mg to 1.75 mg of citric acid;
   c) from 2.25 mg to 2.65 mg of disodium hydrogen phosphate;
   d) from 0.05 mg to 0.20 mg of benzalkonium chloride; and
   e) sodium chloride in an amount sufficient to provide said composition with an osmotic pressure comparable to that of human plasma.

19. The stable, aqueous composition of claim 1, wherein said buffering agent can also function as said osmotic pressure-controlling agent.

20. The stable, aqueous composition of claim 1, wherein said buffering agent in combination with sodium chloride can also function as said osmotic pressure-controlling agent.

21. The aqueous composition of claim 11, wherein said buffering agent can also function as said osmotic pressure-controlling agent.

22. The aqueous composition of claim 11, wherein said buffering agent in combination with sodium chloride can also function as said osmotic pressure-controlling agent.

* * * * *

UNITED STATES PATENT AND TRADEMARK OFFICE
CERTIFICATE OF CORRECTION

PATENT NO. : 5,482,931

DATED : January 9, 1996

INVENTOR(S) : Alan Harris and Birgitta Tennhammar-Ekman

It is certified that error appears in the above-identified patent and that said Letters Patent is hereby corrected as shown below:

In claim 11, column 6, line 50, delete "of" and substitute therefor --or--; and in column 6, line 51 delete "the" and substitute therefor --that--.

Signed and Sealed this

Sixth Day of May, 1997

*Attest:*

BRUCE LEHMAN

*Attesting Officer*    Commissioner of Patents and Trademarks